United States Patent

Kataoka et al.

[11] Patent Number: 5,925,720
[45] Date of Patent: Jul. 20, 1999

[54] HETEROTELECHELIC BLOCK COPOLYMERS AND PROCESS FOR PRODUCING THE SAME

[75] Inventors: Kazunori Kataoka, 1083-4, Ohmuro, Kashiwa-shi, Chiba 277, Japan; Carmen Scholz, Lowell, Mass.; Michihiro Iijima, Chiba, Japan; Takahito Kutsuna, Ibaraki, Japan; Yukio Nagasaki, Ibaraki, Japan; Masao Kato, Ibaraki, Japan; Teruo Okano, Chiba, Japan

[73] Assignee: Kazunori Kataoka, Kashiwa, Japan

[21] Appl. No.: 08/930,898

[22] PCT Filed: Apr. 18, 1996

[86] PCT No.: PCT/JP96/01057

§ 371 Date: Dec. 18, 1997

§ 102(e) Date: Dec. 18, 1997

[87] PCT Pub. No.: WO96/33233

PCT Pub. Date: Oct. 24, 1996

[30] Foreign Application Priority Data

Apr. 19, 1995 [JP] Japan .................................. 7-93928

[51] Int. Cl.$^6$ .......................... C08G 63/08; C08G 63/66; C08G 65/26; C08G 65/32
[52] U.S. Cl. .......................... 525/523; 525/922; 424/450
[58] Field of Search ..................... 525/523, 922; 424/450

[56] References Cited

U.S. PATENT DOCUMENTS 5,153,297 10/1992 Munzmay et al. .
5,410,016 4/1995 Hubbell et al. .

FOREIGN PATENT DOCUMENTS 5-117359 5/1993 Japan .
6-508831 10/1994 Japan .

OTHER PUBLICATIONS

English Abstract—International Publication No. WO 93/00101
International Search Report of PCT/JP96/01057

Primary Examiner—Nathan M. Nutter
Attorney, Agent, or Firm—Scully, Scott, Murphy & Presser

[57] ABSTRACT

This invention provides a heterotelechelic oligomer or polymer which is represented by formula below:

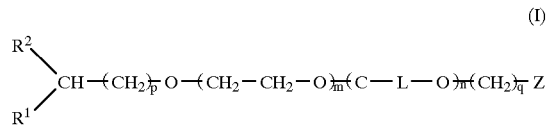

(I)

wherein $R^1$ and $R^2$ form an acetal, or, combined with each other, denote oxy (=O), p, m, n and q each denote a certain integer, L is a group which forms an ester, and Z denotes a certain functional group.

This invention a so provides a process to produce the above oligomer or polymer by means of living polymeri-zation. Since this oligomer or polymer forms a high- molecular micelle which is stable in an aqueous solvent, said oligomer or polymer will be useful as a carrier for drug delivery.

13 Claims, 8 Drawing Sheets

HETEROTELECHELIC BLOCK COPOLYMERS AND PROCESS FOR PRODUCING THE SAME

This application is filed under 35 USC 371 as PCT/JP96/01057, filed Apr. 18, 1996 under 37 USC 371.

FIELD OF THE INVENTION

The present invention relates to a heterotelechelic block copolymer which has different functional groups on its both ends, a method for the production thereof and its application to high-molecular micelle. More detailedly, this invention discloses a polymer which has different functional groups on its both ends while having, in its main chain, polyethylene oxide as a hydrophilic segment and polyester as a hydrophobic segment.

In this invention, the term "polymer" includes oligomer.

PRIOR ARTS

A high-molecular micelle or nanosphere composed of a hydrophilic/hydrophobic type block copolymer wherein a hydrophilic polymer like polyethylene oxide is combined with a hydrophobic polymer at the molecular level is now attracting attention as a carrier for drug delivery or the like. Said high-molecular micelle and nanosphere have been prepared from a hydrophilic/hydrophobic type block copolymer wherein a hydrophilic polymer is combined with a hydrophobic polymer at the molecular level.

In conventional processes to produce a hydrophilic/hydrophobic type block copolymer, however, there is a limitation on the species of terminal functional groups introduced, and there have only been proposed block copolymers whose functional groups are restricted to methoxy and hydroxyl groups. If one succeeded in introducing optional functional groups onto the micelle surface at an optional proportion, it would become possible to provide a functional high-molecular micelle which could useful for drug delivery to certain organs.

The object of this invention is to provide a block copolymer, which has different functional groups on its both ends, as a polyfunctional polymer which is capable of forming a high-molecular micelle.

DISCLOSURE OF INVENTION

The inventors of this invention have found out that there can easily be produced a block copolymer which has a protected or non-protected aldehyde group on one and of molecule and various functional groups on the other end, when an alkylene derivative having a certain kind of aldehyde group and a hydroxyl group is utilized as a living polymerization initiator and when ethylene oxide and lactide or lactone are polymerized as monomers.

They have also confirmed that a block copolymer obtained in this manner forms a high-molecular micelle which is quite stable in an aqueous solvent.

This invention provides a heterotelechelic block copolymer which has different functional groups on both ends of molecule and which is represented by formula (I) below:

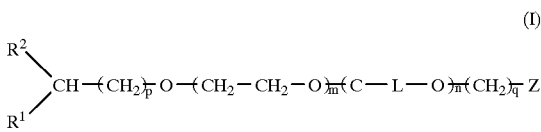

(I)

wherein $R^1$ and $R^2$ independently denote $C_{1-10}$ alkoxy, aryloxy or aryl-$C_{1-3}$ alkyloxy, or $R^1$ and $R^2$, combined with each other, denote ethylenedioxy (—O—CH(R')—CH$_2$—O—: wherein R' denotes hydrogen atom or $C_{1-6}$ alkyl) which may be substituted with $C_{1-6}$ alkyl, or, combined with each other, denote oxy (=O), L denotes

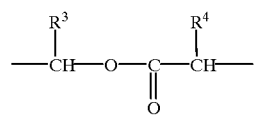

or -(CH$_2$)$_r$- wherein $R^3$ and $R^4$ independently denote hydrogen atom, $C_{1-10}$ alkyl, aryl or aryl-$C_{1-3}$ alkyl, and r denotes an integer of 2–5, m denotes an integer of 2–10,000, n denotes an integer of 2–10,000, p denotes an integer of 1–5, q denotes an integer of 0–20, Z denotes, when q is 0 (zero), hydrogen atom, alkali metal acetyl, acryloyl, methacryloyl, cinnamoyl, p-toluenesulfonyl, 2-mercaptopropionyl or 2-aminopropionyl, or allyl or vinylbenzyl, while, when q is an integer of 1–20, denoting $C_{1-6}$ alkoxycarbonyl, carboxyl, mercapto or amino.

As another aspect, this invention provides a process to produce the block copolymer of the above formula (I) which process comprises the following steps:

Step (1)

A polymerization initiator represented by the following formula (II)

(II)

wherin $R^{1-1}$ and $R^{2-1}$ independently denote $C_{1-10}$ alkoxy, or, $R^{1-1}$ and $R^{2-1}$, combined with each other, denote ethylenedioxy which may be substituted with $C_{1-6}$ alkyl, p denotes an integer of 1–5 and M denotes alkali metal is made to react with ethyleneoxide so that a compound represented by the following formula (II) may be produced:

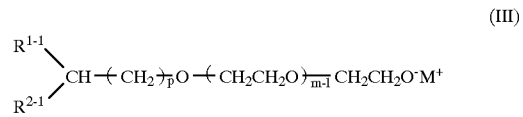

(III)

wherein $R^{1-1}$, $R^{2-1}$, p and M are as defined in formula (II), and m denotes an integer of 2–10,000.

Step (2)

The compound of formula (II) is allowed to react with lactide or lactone which is represented by the following formula (III-a) or (III-b):

$$R^3-CH\begin{matrix}O\\|\\O=C\end{matrix}\begin{matrix}\\O\\|\end{matrix}\begin{matrix}C=O\\|\\CH-R^4\end{matrix}\qquad(\text{III-a})$$

or $$\begin{matrix}O\\(CH_2)_r\end{matrix}C=O\qquad(\text{III-b})$$

wherein $R^3$ and $R^4$ independently denote hydrogen atom, $C_{1-10}$ alkyl, aryl or aryl-$C_{1-3}$ alkyl, and r denotes an integer of 2–5, so that a block copolymer represented by the following formula (IV) may be formed:

$$\begin{matrix}R^{1-1}\\\\R^{2-1}\end{matrix}CH-(CH_2)_p O-(CH_2CH_2O)_{\overline{m}}(\underset{\underset{O}{\|}}{C}-L-O)_{\overline{n-1}}\underset{\underset{O}{\|}}{C}-L-O^-M^+\qquad(\text{IV})$$

wherein

L denotes $$\begin{matrix}R^3 & & R^4\\| & & |\\-CH-O-\underset{\underset{O}{\|}}{C}-CH-\end{matrix}$$

or $-(CH_2)_r-$ and $R^{1-1}$, $R^{2-1}$, p, m, n and M are as defined above.

The above step provides a living polymer of this invention (which is included in the polymer of formula (I)) which is usable as an intermediate for further extending some polymer segment or other.

Step (3)

(i) The alkali metal alkoxide of formula (IV) is selectively hydrolyzed to form a block copolymer of the following formula (V)

$$\begin{matrix}R^{1-1}\\\\R^{2-1}\end{matrix}CH-(CH_2)_p O-(CH_2CH_2O)_{\overline{m}}(\underset{\underset{O}{\|}}{C}-L-O)_{\overline{n}}H\qquad(\text{V})$$

wherein $R^{1-1}$, $R^{2-1}$, p, m, L and n are as defined above; or (ii) the block copolymer of formula (IV) is completely hydrolyzed to form a block copolymer of the following formula (VI)

$$\begin{matrix}O\\\\\\H\end{matrix}CH-(CH_2)_p O-(CH_2CH_2O)_{\overline{m}}(\underset{\underset{O}{\|}}{C}-L-O)_{\overline{n}}H\qquad(\text{VI})$$

wherein p, m, n and L are as defined above.

The above steps provide a block copolymer of this invention which has a protected aldehyde group or an aldehyde group itself at the α-terminal of molecule, and a hydroxyl group at the ω-terminal.

Step (4)

The block copolymer of formula (V) which has a protected aldehyde group at the α-terminal of molecule is allowed to react with (i) acetic acid, acrylic acid, methacrylic acid, cinnamic acid or p-toluenesulfonic acid, or a reactive derivative thereof, or (ii) allyl halide or vinylbenzyl halide, or (iii) a halide represented by the following formula (VII)

$$X-(CH_2)_{q'}Z'\qquad(\text{VII})$$

wherein X is chlorine, bromine or iodine, q' is an integer of 1–20 and Z' is $C_{1-6}$ alkoxycarbonyl or a protected amino, to form block copolymers of this invention each of which has a corresponding functional group other than hydroxyl group at the ω-terminal of molecule.

Step (5)

The p-toluenesulfonic ester obtained in (i) of Step (4) can be further converted, by means of transesterification, into a block copolymer having another functional group (e.x., mercapto or amine) at the ω-terminal. The block copolymer which has an aldehyde-protecting group or a carboxyl-protecting group and which has been produced through the above steps can be converted, by means of hydrolysis reaction, into the block copolymer of this invention wherein one of the protecting groups or all the protecting groups are eliminated.

As another aspect, this invention provides a high-molecular micelle with use of the block copolymer of formula (I).

A part of thus obtained heterotelechelic polymer of this invention can be used as a precursor for the production of another polymer. As will be seen from their constituent components, these polymers are expected to have bio-affinity and high bioavailability. They can therefore be used for materials directly applied to living organism such as carrier for drug delivery. Moreover, in accordance with the third aspect, this invention provides a high-molecular micelle which is quite stable in an aqueous solvent. The polymer of this invention is therefore useful also for drug delivery to a certain organ.

BRIEF EXPLANATIONS OF DRAWINGS

FIG. 1 is a gel permeation chromatogram of acetal α-terminal/hydroxy ω-terminal polyester oxide/polylactide block copolymer (the sample of Example 1).

Operational condition: TSK-Gel (G4000HXL, G3000HXL, G2500HXL)

Eluent: THF (containing 2% triethyl amine)

Flow rate: 1 ml/min.

DETAILED DESCRIPTION OF THE INVENTION

Figure 1:
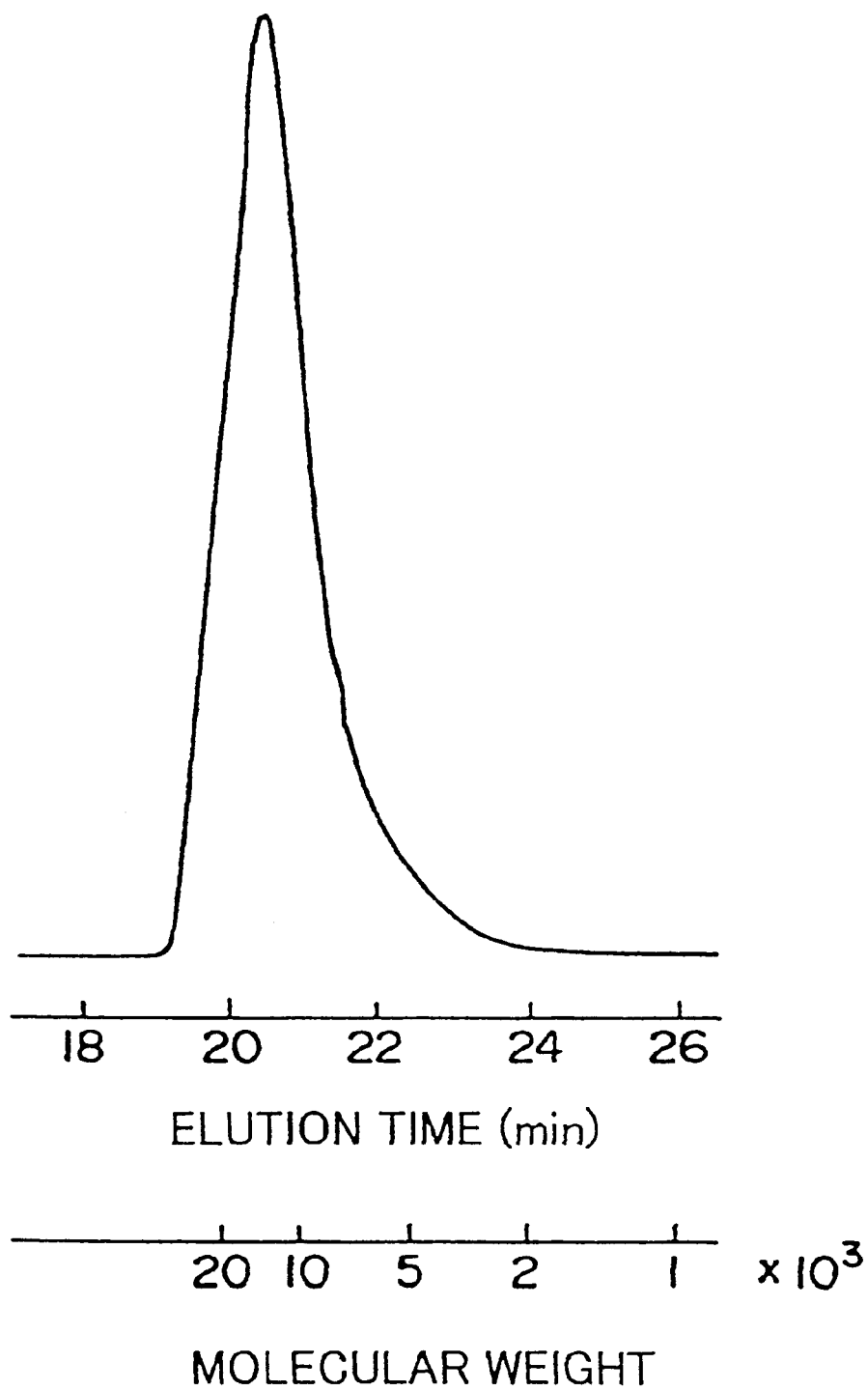

The alkyl portion of alkoxy and alkyl in the invention mean straight chain- or branched-alkyl group. Therefore, the alkyl portion of $C_{1-10}$ alkoxy or $C_{1-10}$ alky in formula (II) and formula (III-a) include methyl, ethyl, propyl, iso-propyl, butyl, sec-butyl, tert-butyl, pentyl, iso-pentyl, hexyl, 2-methyl pentyl, 3-methyl, pentyl, octyl, 2-ethyhexyl, decyl and 4-propyl pentyl. In these, the alkyl portion in the alkoxy of $R^1$ and $R^2$ is preferably $C_{1-6}$ alkyl, in particular $C_{1-3}$ alkyl.

Especially preferable examples of alkoxy of $R^1$ and $R^2$ therefore include methoxy, ethoxy, propoxy and isopropoxy. Examples of $R^1$ and $R^2$ include aryl, especially phenyl, and aryl-$C_{1-3}$ alkyl, especially benzyl or phenethyl. These groups may be similar or different, but is preferably similar. Although $R^1$ and $R^2$ may denote, combined with each other, ethylenedioxy (—O—CH(R')—CH$_2$—O—: wherein R' denotes hydrogen atom or $C_{1-6}$ alkyl) which may be substituted with $C_{1-6}$ alkyl, they are preferably ethylenedioxy, propylenedioxy or 1, 2-butylenedioxy.

When hydrolyzed, $R^1$ and $R^2$ of these groups are conveniently combined with each other to form oxy (=O), or, in other words, to form the block copolymer of this invention which has an aldehyde group at the α-terminal of the molecule.

The mark "p" in formula (I) denotes an integer of 1–5. In view of the fact that the segment

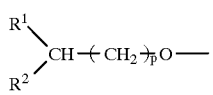

is derived from the polymerization initiator (See: formula (II)) in the process of this invention, $R^1$, $R^2$ and p are preferably selected so that said segment constitutes en bloc an acetal group such as dimethoxymethoxy, 2, 2-dimethoxyethoxy, 3, 3-dimethoxypropoxy, 4, 4-dimethoxybutoxy, diethoxymethoxy, 2, 2-diethoxyethoxy, 3, 3-diethoxypropoxy, 4, 4-diethoxybutoxy, dipropoxymethoxy, 2, 2-dipropoxyethoxy, 3, 3-dipropoxypropoxy or 4, 4-dipropoxybutoxy.

$R^3$ and $R^4$ may denote any of hydrogen atom, $C_{1-10}$ alkyl, aryl or aryl-$C_{1-3}$ alkyl so long as they are useful for the object of this invention. Preferable, however, are hydrogen atom (derived from glutaric acid) and methyl (derived from lactic acid) from the viewpoint of bioavailability.

According to the production process by means of living polymerization of this invention, the mark "m" in formula (I) may theoretically take any figure if the amount ratio of ethylene oxide (monomer) to polymerization initiator is adjusted. In order to fulfill the object of this invention, however, m is preferably an integer of 2–10,000. In order that this segment may give hydrophilicity to the block copolymer of this invention, m is preferably an integer at least 10. For the purpose of easily adjusting the molecular weight distribution of this segment narrow and providing a block copolymer having excellent bioavailability, m is an integer of at most 500, preferably at most 200.

As for "n" which defines the molecular weight of polyester segment of formula (I), optimal number varies depending on the property of the groups $R^3$ and $R^4$ as will be seen from the fact that this segment mainly imparts hydrophobicity to the block copolymer of this invention. Following the polymerization process of this invention, n can take any number in the same manner as in the case of polyethylene oxide segment. The number of n is therefore not restricted. However, it is normally 2–10,000.

Moreover, in order to keep hydrophilicity/hydrophobicity balance well against polyethylene oxide segment, m preferably takes an integer of 10–200, in particular 10–100.

The segment —(CH$_2$)$_q$—Z of formula (I) mainly specifies the functional group (or reactive group) at ω-terminal of the block copolymer of this invention. When q is 0 (zero) (i.e., the case where Z is directly bound to oxygen atom at the ω-position of the polyester segment), Z can be an alkali metal. In this case, the polymer of this invention can be a living polymer Since such a polymer of this invention can act as an initiator for further living polymerization, it is usefull as a precursor for various kind of polymers. From this viewpoint, examples of alkali metal include sodium, potassium and cesium.

The above living polymer is ready to provide a polymer wherein Z denotes hydrogen atom (or a polymer which has hydroxyl group at the ω-position) since the alcoholate portion of the living polymer is easily hydrolyzed. Said hydroxyl group can further be converted into other functional groups by means of various reactions such as esterification or etherification. Thus, when q is 0 Z can be acetyl (—COCH$_3$), acryloyl (—COCH=CH$_2$), methacryloyl (—COC(CH$_3$)=CH$_2$), cinnamoyl

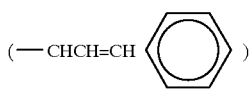

and p-toluenesulfonyl

and, further, can be allyl ($-CH_2-CH=CH_2$) and vinyl-benzyl

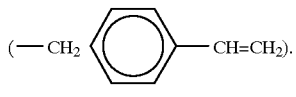

When these functional groups have ethylenically unsaturated bond, pendant type polymers can be derived with use of said bond. When Z denotes p-toluenesulfonyl group, it can be converted by a known method into other functional group with use of transesterification. Z can therefore be 2-mercaptopropionyl or 2-aminopropionyl.

When q is an integer of 1–20, preferably 1–4, especially preferably 2, the segment $-(CH_2)_q-Z$ denotes en bloc, for example, $C_{1-6}$ alkoxy (e.x., methoxy, ethoxy or propoxy) carbonyl-methyl, -ethyl or -propyl, or 2-aminoethyl, carboxy-methyl, -ethyl or -propyl.

Table 1 below shows examples of block copolymer of this invention which the above substitutes (or segments) are combined with one another to constitute.

TABLE 1

$$\begin{array}{c} R^1 \\ \phantom{R^1}\diagdown \\ \phantom{R^1}CH-(CH_2)_p-O-(CH_2CH_2O)_m-(\underset{\underset{O}{\|}}{C}-L-O)_n-(CH_2)_q-Z \\ \phantom{R^1}\diagup \\ R^1 \end{array}$$ (I)

| Compound No | $R^1$ | $R^2$ | p | m*[1] | L | n*[2] | $-(CH_2)_q-Z$ |
|---|---|---|---|---|---|---|---|
| 1 | $CH_3CH_2O$ | $CH_3CH_2O$ | 2 | 280 | $-CHOCCH-$ with $CH_3$, $CH_3$ branches and $\|O$ | 40 | H |
| 2 | $CH_3CH_2O$ | $CH_3CH_2O$ | 2 | 280 | $-CHOCCH-$ with $CH_3$, $CH_3$ branches and $\|O$ | 40 | K |
| 3 | $CH_3CH_2O$ | $CH_3CH_2O$ | 2 | 280 | $-CHOCCH-$ with $CH_3$, $CH_3$ branches and $\|O$ | 70 | H |
| 4 | $CH_3CH_2O$ | $CH_3CH_2O$ | 2 | 280 | $-CHOCCH-$ with $CH_3$, $CH_3$ branches and $\|O$ | 70 | K |
| 5 | $CH_3CH_2O$ | $CH_3CH_2O$ | 2 | 280 | $-CHOCCH-$ with $CH_3$, $CH_3$ branches and $\|O$ | 70 | $COCH=CH_2$ |

TABLE 1-continued $$R^1_2CH-(CH_2)_p-O-(CH_2CH_2O)_m-C(=O)-L-O-_n(CH_2)_q-Z \quad (I)$$

| Compound No | $R^1$ | $R^2$ | p | m*1) | L | n*2) | $-(CH_2)_q-Z$ |
|---|---|---|---|---|---|---|---|
| 6 | $CH_3CH_2O$ | $CH_3CH_2O$ | 2 | 280 | $-CH(CH_3)OC(=O)CH(CH_3)-$ | 70 | $COC(CH_3)=CH_2$ |
| 7 | $CH_3CH_2O$ | $CH_3CH_2O$ | 2 | 280 | $-CH(CH_3)OC(=O)CH(CH_3)-$ | 70 | $CH_2$-C$_6$H$_4$-CH=CH$_2$ |
| 8 | $CH_3CH_2O$ | $CH_3CH_2O$ | 2 | 280 | $-CH(CH_3)OC(=O)CH(CH_3)-$ | 70 | $SO_2$-C$_6$H$_4$-CH$_3$ |
| 9 | $CH_3CH_2O$ | $CH_3CH_2O$ | 2 | 280 | $-CH(CH_3)OC(=O)CH(CH_3)-$ | 70 | $CO-CH(CH_3)SH$ |
| 10 | $CH_3CH_2O$ | $CH_3CH_2O$ | 2 | 280 | $-CH(CH_3)OC(=O)CH(CH_3)-$ | 70 | $COCH(CH_3)NH_2$ |
| 11 | $CH_3CH_2O$ | $CH_3CH_2O$ | 2 | 280 | $-CH(CH_3)OC(=O)CH(CH_3)-$ | 70 | $COCH_3$ |
| 12 | $CH_3CH_2O$ | $CH_3CH_2O$ | 2 | 100 | $-CH(CH_3)OC(=O)CH(CH_3)-$ | 70 | H |
| 13 | $CH_3O$ | $CH_3O$ | 2 | 100 | $-CH(CH_3)OC(=O)CH(CH_3)-$ | 70 | H |
| 14 | $CH_3CH_2O$ | $CH_3CH_2O$ | 2 | 100 | $-(CH_2)_4-$ | 50 | H |
| 15 | $CH_3CH_2O$ | $CH_3CH_2O$ | 2 | 100 | $-(CH_2)_4-$ | 50 | K |
| 16 | $CH_3CH_2O$ | $CH_3CH_2O$ | 2 | 100 | $-(CH_2)_4-$ | 50 | $COCH=CH_2$ |

TABLE 1-continued $$\underset{R^1}{\overset{R^1}{\diagdown}}CH-(CH_2)_p-O-(CH_2CH_2O)_m-(\underset{\underset{O}{\parallel}}{C}-L-O)_n-(CH_2)_q-Z \quad (I)$$

| Compound No | $R^1$ | $R^2$ | p | m*1) | L | n*2) | $-(CH_2)_q-Z$ |
|---|---|---|---|---|---|---|---|
| 17 | CH³CH₂O | CH₃CH₂O | 2 | 100 | $-(CH_2)_4-$ | 50 | COC(CH₃)=CH₂ |
| 18 | O= | | 2 | 280 | $-CHOCCH-$ with CH₃, CH₃ substituents and C=O | 40 | H |
| 19 | O= | | 2 | 100 | $-CHOCCH-$ with CH₃, CH₃ substituents and C=O | 70 | H |
| 20 | O= | | 2 | 100 | $-CHOCCH-$ with CH₃, CH₃ substituents and C=O | 70 | COCH=CH₂ |
| 21 | O= | | 2 | 100 | $-CHOCCH-$ with CH₃, CH₃ substituents and C=O | 70 | COC(CH₃)=CH₂ |
| 22 | O= | | 2 | 100 | $-CHOCCH-$ with CH₃, CH₃ substituents and C=O | 70 | CH₂–C₆H₄–CH=CH₂ |
| 23 | O= | | 2 | 100 | $-CHOCCH-$ with CH₃, CH₃ substituents and C=O | 70 | COCH₃ |
| 24 | O= | | 3 | 100 | $-CHOCCH-$ with CH₃, CH₃ substituents and C=O | 70 | H |
| 25 | O= | | 2 | 100 | $-(CH_2)_4-$ | 50 | H |
| 26 | O= | | 2 | 100 | $-(CH_2)_4-$ | 50 | COCH=CH₂ |
| 27 | O= | | 2 | 100 | $-(CH_2)_4-$ | 50 | COC(CH₃)=CH₂ |

*1) and *2) show values calculated from number average molecular weight.

The above-mentioned heterotelechelic block copolymer which is to be provided by this invention is produced efficiently by the production process of this invention which is shown by the following reaction schemes.

polyethylene oxide segment is added. Compound (A) can be obtained by treating acetal-protected alcohol with a metallizing agent such as alkali metal like sodium and potassium; organic metal like sodium naphthalene, potassium

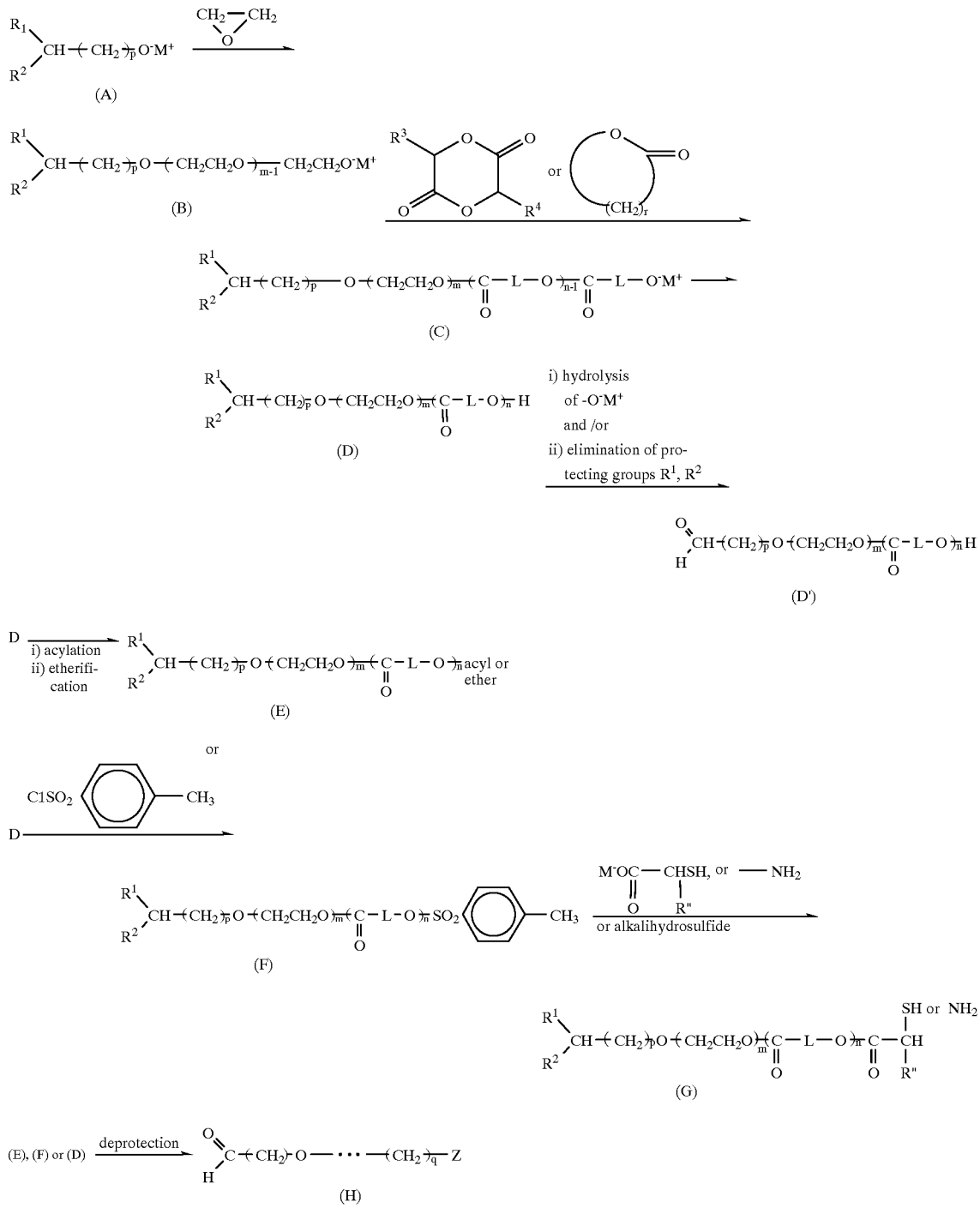

Production of (B) of from (A):

Alkali metal acetal-protected a alkoxide (A) is made to react with ethylene oxides to form compound (B) to which naphthalene, cumylpotassium and cumylcesium; or metal hydride like sodium hydride or potassium hydride.

The above reaction from (A) to (B) is made to occur without solvent, or preferably in an anhydrous aprotic solvent, and at a temperature in a broad range, e.x. −50° C.–300° C., preferably 10° C.–60° C., conveniently at a room temperature (20° C.–30° C.) The reaction may be conducted either under pressure or under reduced pressure. Examples of solvent used include, not restrictively, benzene, toluene, xylene, tetrahydrofuran, dioxane and acetonitrile. Examples of reactor include not restrictively, round flask, autoclave and pressure sealed tube. Reactor is preferably sealed airtight, and is more preferably filled with inert gas. The concentration of reaction liquid is 0.1 to 95% by weight, preferably 1 to 80% by weight, most preferably 3 to 10% by weight.

Production of (C) from (B):

A reaction mixture containing (B) is allowed to react with lactide or lactone to form a living block copolymer (C) wherein polyester segment is added via ω-terminal hydroxyl group of polyethylene oxide. The condition of this reaction can be almost the same as the above reaction from (A) to (B). Usable lactide or lactone is capable of forming such a chain as has been defined with regard to $R^3$ and $R^4$ of L of formula (I). Examples of preferable lactide include, not restrictively, lactide of lactic acid and lactide of glycolic acid. Examples of usable lactone, on the other hand, include β-propiolactones, γ-butyrolactone, δ-valerolactone and ε-caprolactone. Among these, γ-butyrolactone and δ-valerolactone are preferable from the viewpoint of easy reactivity.

In the above steps, the proportion of polymerization initiator to ethylene oxide, lactide or lactone is, in molar ratio, 1:1 to 1:10,000, more preferably 1:5 to 1:10,000, most preferably 1:10–200 to 1:50–200.

The process of this invention not only makes it possible to adjust molecular weight of each segment according to the ratio of monomer used to polymerization initiator, but also provides a mono-dispersed or mono-modal block copolymer wherein each of the formed segments has a very narrow molecular weight distribution.

The living polymer (C) itself which is obtained in the above manner is included in the polymer of this invention. The alcoholate (C), however, can be converted (i) into polymer (D) by partial hydrolysis under a moderate condition (i.e., only adding water), or (ii) into polymer (D') which has an aldehyde group at α-terminal and a hydroxyl group at ω-terminal by means of treating (C) under a condition wherein acetal can be simultaneously hydrolyzed. The latter hydrolysis can be carried out with use of acids such as trifluoroacetic acid, hydrochloric acid, sulfuric acid, nitric acid, formic acid and hydrogen fluoride, or alkalis such as sodium hydroxide and potassium hydroxide, and, if necessary, with heating.

Production of (E)–(G) from (D):

(D) is made to react with (i) acetic acrylic acid, methacrylic acid or p-toluenesulfonic acid to form an ω-terminal acyl compound, or (ii) a halide represented by formula (V)

$$\text{halo}-E \quad\quad (V)$$

wherein halo and E in formula (V) correspond to groups other than acyl group in $-\!(\!CH_2\!)_q\!Z$ in formula (I)

to form an ω-terminal ether compound.

The above reactions can be conducted by known esterification or etherification process. As for organic acid in the above (i), it is convenient to use a reactive derivative of organic acid such as acid anhydride and acid halide.

When a mercapto group is to be introduced onto the ω-terminal, it is useful to make a p-toluenesulfonated compound (F) react with an electrophilic agent such as thiosodium acetate, thiopotassium acetate or potassium hydrosulfide so that a thioester group may be introduced onto the ω-terminal, and thereafter to treat said thioester group with acid or alkali and, then, there can be obtained a polymer represented by (G).

When an amino group is to be introduced onto the ω-terminal, it is useful to hydrolyze (D) with use of an electraphilic agent such as N-(2-bromoethyl)-phtalimide, N-(3-bromopropyl)phthalimide, 1-bromo-2-(benzenamino) ethane or N-(2-bromoethyl)benzyl carbamate, and thereafter to conduct an alkali or acid treatment so as to eliminate the groups $R^1$ and $R^2$ and to simultaneously hydrolyze ω-terminal imide bond, and, thus, there can be obtained a polymer which has an amino group at ω-terminal.

Elimination of the groups $R^1$ and $R^2$ from polymers (D), (E), (F) and (G) for the purpose of obtaining α-terminal aldehyde can be conducted by the above-mentioned conversion from (C) to (D'). As for the recovery of polymer from the reaction liquid, it can be carried out by solvent precipitation of the polymer per se, gel filtration chromatography, dialysis, ultrafiltration or the like.

In this manner, there can be obtained various kind of heterotelechelic block copolymers represented by formula (I) of this invention. The obtained polymer (except living polymer) is capable of forming a high-molecular micelle which is very stable in an aqueous solvent.

This high-molecular micelle can be prepared by, for example, subjecting a polymer solution or suspension to a heating treatment, an ultrasonification treatment and an organic solvent treatment, separately or in combination. Heating treatment is conducted by dispersing or dissolving a mixture of one or more species of block copolymers of this invention in water at a temperature ranging from 30–100° C., more preferably 30–500° C. Ultrasonification is conducted by dispersing a mixture of one or more species of block copolymers in water in a range from 1W to 20W for one second to 24 hours, preferably in a range from 1W to 3W for three hours.

Organic solvent treatment is conducted by dissolving a mixture of one or more species of block copolymers in an organic solvent, dispersing the resulting solution in water and thereafter evaporating the organic solvent. Examples of the organic solvent include chloroform, benzene, toluene, methylene chloride, etc.

It is also possible to prepare the high-molecular micelle of this invention by dissolving said mixture in methanol, ethanol, tetrahydrofuran, dioxane, dimethylsulfoxide, dimethylformamide or the like, and thereafter dialyzing the resulting solution against an aqueous solvent. The fractional molecular weight of the membrane used for the dialysis is not restricted since optimal value varies according to the molecular weight of block copolymer to be treated. Generally, however, the fractional molecular weight is at most 1,000,000, preferably 5,000–20,000.

As an aqueous solvent, there can be employed water and buffer solution. The proportion of the aqueous solution used to the above organic solvent in dialysis is generally 1 to 1000 times, preferably 10 to 100 times. Temperature is not restricted in particular. Normally, the treatment is conducted at 5–25° C.

Thus produced high-molecular micelle of this invention has a critical micelle concentration as low as 4–12 mg/l, and is much more stable in an aqueous solvent than low-molecular micelle such as liposome which has widely been given consideration as a carrier for drug delivery. This means that, when administered into blood, the high-molecular micelle of this invention is expected to significantly increase in half-life in blood, and, thus, it can be said that the polymer of this invention has excellent properties as a carrier for drug delivery.

Below, this invention is explained in more detail with the working examples, but these working examples do not limit the area covered by this invention in any way.

EXAMPLE 1

THF 20 ml, 3, 3-diethoxypropanol 0.15 g, and a potassium naphthalene 0.5 mol/L-tetrahydrofuran solution 2 ml was added to the reaction container and agitated for 3 minutes in an argon atmosphere; a potassium compound of 3, 3-diethoxypropanol (potassium 3, 3-diethoxypropanoxide) was produced.

Ethyleneoxide 8.8 g was added to this solution and agitated at room temperature and 1 atm. After reacting for two days, lactide 7.2 g was added quantitatively to this reaction solution and then agitated for one hour. This solution was poured into cooled propanol and the polymer produced was precipitated. The precipiate attained through centrifugal separation was refined by freeze drying from benzene. This yield was 15.0 g (94%). The polymer attained through gal permeation chromatography was mono-modal, the molecular weight of the polymer was 16,000 (FIG. 1).

Figure 2:
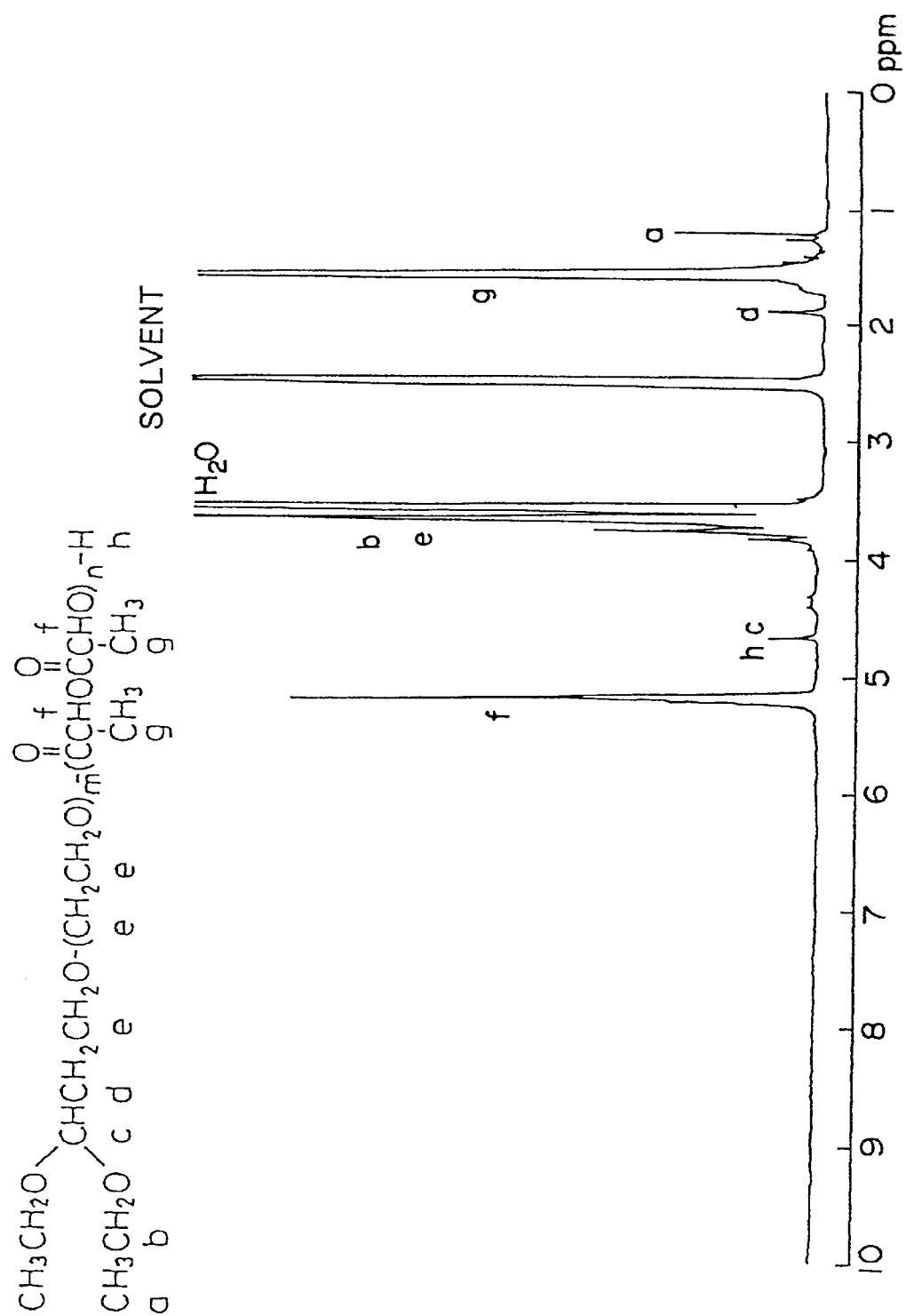
FIG. 2 shows proton nuclear magnetic resonance spectra of acetal α-terminal/hydroxy ω-terminal polyethylene oxide/polylactide block copolymer (the sample of Example 1).

According to the proton nuclear magnetic resonance spectra in the chloroform deuteride of the polymer attained, this polymer was confirmed to be the heterotelechelic oligomer having both units of polyethylene oxide (PEO) and polyactide (PL) and quantitatively having acetal group on the α-terminal and hydroxy group on the ω-terminal (FIG. 2). The number average molecular weight of each segment of the block polymer determined by the integral ratio of the spectra were 8800 for PEO and 7000 for PL.

EXAMPLE 2

THF 20 ml, 3, 3-diethoxypropanol 01.5 g, and a potassium naphthalene 0.5 mol/L-tetrahydrofuran solution 2 ml was added to the reaction container and agitated for 3 minutes in an argon atmosphere; a potassium compound of 3, 3-diethoxypropanol (potassium 3, 3-diethoxypropanoxide) was produced.

Ethylene oxide 5.7 g was added to this solution and agitated at room temperature under 1 atm. After reacting for two days, lactide 7.2 g was added to this reaction solution and agitated for one hour. This solution was poured into cold propanol and the polymer produced was precipitated. The precipitate attained through centrifugal separation was refined by freeze drying from benzene. This yield was 12.4 g (95%). The polymer attained through gel permeation chromatography was mono-modal, the molecular weight of the polymer was about 12,000.

According to the proton nuclear magnetic resonance spectra in the chloroform deuteride of the polymer attained, this polymer was confirmed to be the heterotelechelic oligomer having both units of polyethylene oxide (PEC) and polyactide (PL) and quantitatively having acetal group on the α-terminal and hydroxy group on the ω-terminal. The number average molecular weight of each segment of the block polymer determined by the integral ratio of the spectra were 5400 for (PEO) and 6600 for PL.

EXAMPLE 3

THF 20 ml, 3, 3-diethoxypropanol 0.15 g, and a potassium naphthalene 0.5 mol/L-tetrahydrofuran solution 2 ml was added to the reaction container and agitated for 3 minutes in an argon atmosphere; a potassium compound of 3, 3-diethoxypropanol (potassium 3, 3-diethoxypropanoxide) was produced.

Ethylene oxide 8.8 g was added to this solution and agitated at room temperature under 1 atm. After reacting for two days, δ-valerolactone 5.0 g was added to this reaction solution and agitated for one hour. This solution was poured into cold propanol and the polymer produced was precipitated. The precipitate attained through centrifugal separation was refined by freeze drying from benzene. This yield was 13.5 g (97%). The polymer attained through gel permeation chromatography was mono-modal, the molecular weight of the polymer was about 14,000.

Figure 3:
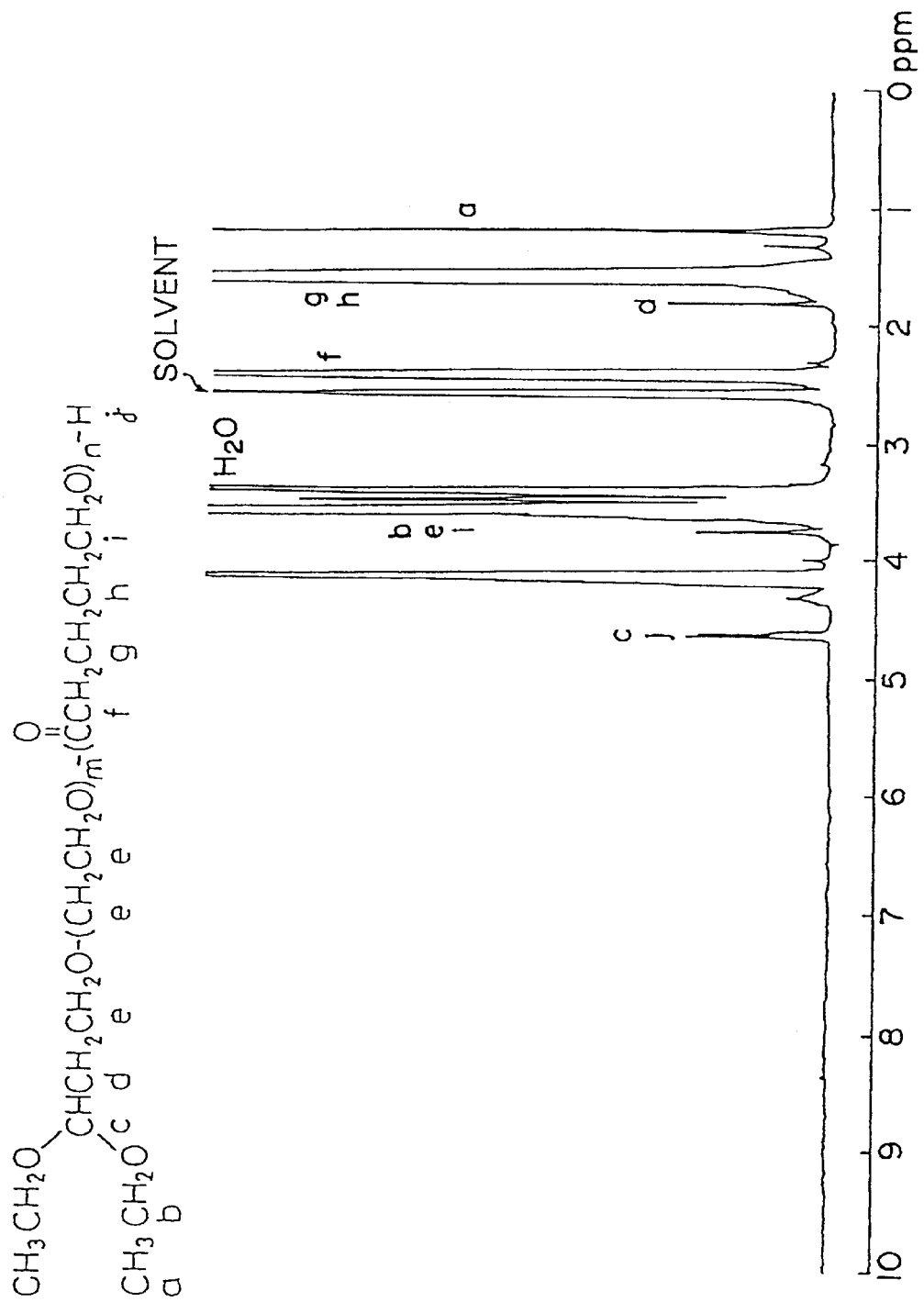
FIG. 3 shows proton nuclear magnetic resonance spectra of acetal α-terminal/hydroxy ω-terminal polyethylene oxide/poly(δ-valerolactone) block copolymer (the sample of Example 3).

According to the proton nuclear magnetic resonance spectra in the chloroform deuteride of the polymer attained, this polymer was confirmed to be the heterotelechelic oligomer having both units of polyethylene oxide (PEO) and poly(δ-valerolactone) (PVL) and quantitatively having acetal group on the α-terminal and hydroxy group on the ω-terminal (FIG. 3). The number average molecular weight of the black polymer determined by the integral ratio of the spectra were 8800 for PEO and 5200 for PVL.

EXAMPLE 4

2.0 mol/L-HCl 50 ml was added to methanol 50 ml in which the block copolymer sample attained in Example 2 was dissolved and this was agitated 1 hour at room temperature. After this solution was neutralized with NaOH aqueous solution, four hours of dialysis (fractional molecular weight 1000) was performed against 20 times the amount of water and this was refined by freeze drying. The yield was 0.85 (85%). The molecular weight of the polymer attained through gel permeation chromatography was confirmed to be unchanged from that before the reaction.

Figure 4:
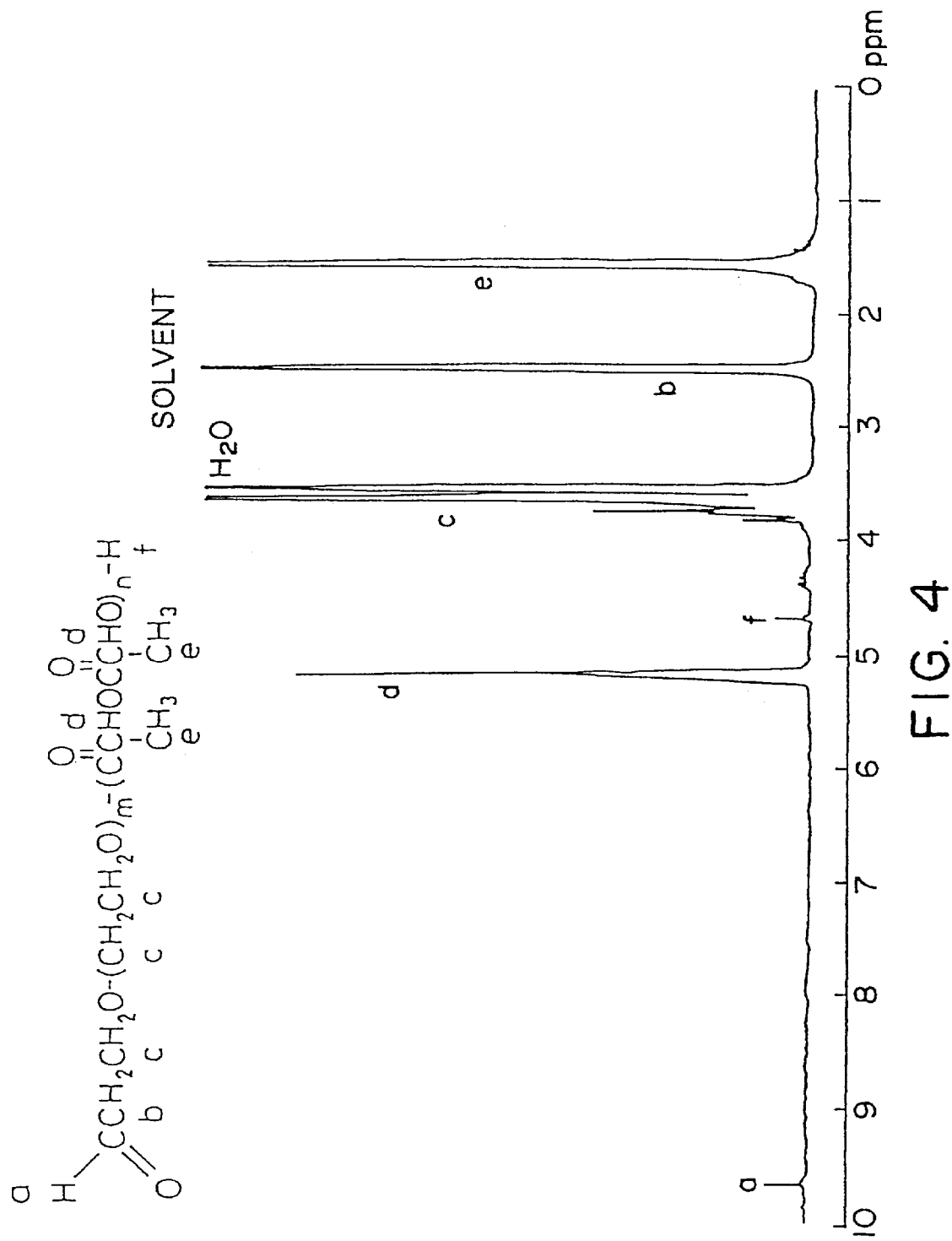
FIG. 4 shows proton nuclear magnetic resonance spectra of aldehyde α-terminal/hydroxy ω-terminal polyethylene oxide/polylactide block copolymer (the sample of Example 4).

According to the proton nuclear magnetic resonance spectra in the chloroform deuteride of the polymer attained, the acetal group disappeared from the α-terminal of this polymer and instead a peak originating with the aldehyde was observed; it was confirmed to be a heterotelechelic PEO/PL oligomer quantitatively having an aldehyde group on the α-terminal and a hydroxy group on the ω-terminal (FIG. 4).

EXAMPLE 5

Pyridine 20 ml and methacrylic anhydride 1.0 g were added to chloroform 20 ml in which 1.0 g of the block copolymer sample attained in Example 2 was dissolved and this was agitated 24 hours at room temperature. This solution was neutralized and rinsed with a hydrochloric acid aqueous solution. The chloroform phase was poured into cold propanol and the polymer was precipitated. The precipitate attained through centrifugal separation was refined by freeze drying from benzene. This yield was 0.8 g (80%). The molecular weight of the polymer attained through gel permeation chromatography was confirmed to be unchanged from before the reaction.

Figure 5:
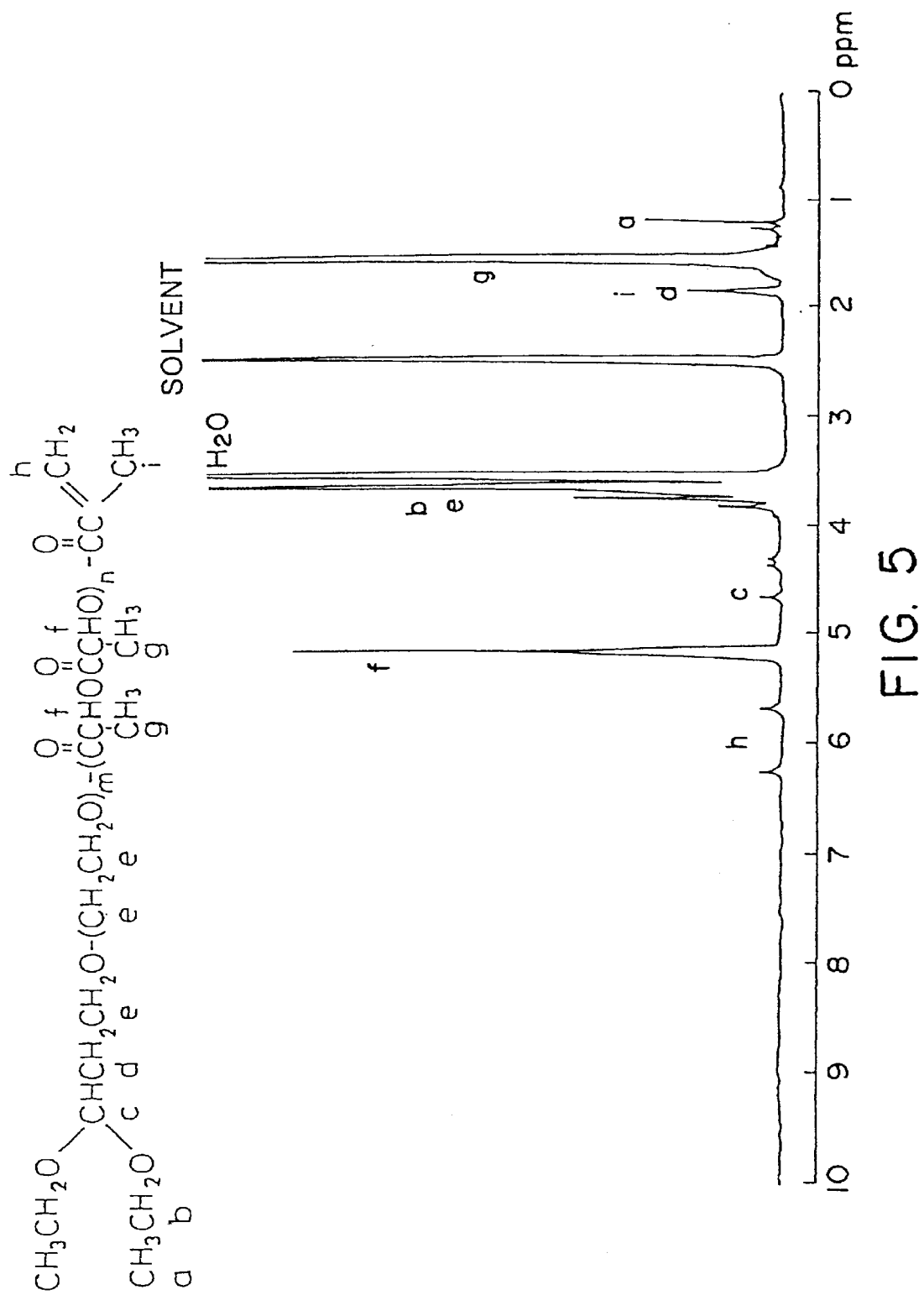
FIG. 5 shows carbon nuclear magnetic resonance spectra of acetal α-terminal/methacryloyl ω-terminal polyethylene oxide/polylactide block copolymer (the sample of Example 5).

According to the carbon nuclear magnetic resonance spectra in the chloroform deuteride of the polymer attained, the peak originating with the hydroxy group an the ω-terminal of this polymer disappeared completely and instead a peak derived from the methacryloyl group was expressed, the polymer was confirmed to be a heterotelechelic PEO/PL oligomer quantitatively having an acetal group on the α-terminal and a methacryloyl group on the ω-terminal (FIG. 5).

EXAMPLE 6

Potassium naphthalene 0.5 mol/L-tetrahydrofuran solution 2 ml and allyl bromide 5 ml were added to tetrahydrofuran 20 ml in which the block copolymer 1.0 g attained in Example 2 was dissolved and agitated for four hours at room temperature. The reaction product attained was poured into cold propanol and the polymer was precipitated. The precipitate attained through centrifugal separation was refined by freeze drying from benzene. This yield was 0.98 g (98%). The molecular weight of the polymer attained through gel permeation chromatography was confirmed to be unchanged from before the reaction.

Figure 6:
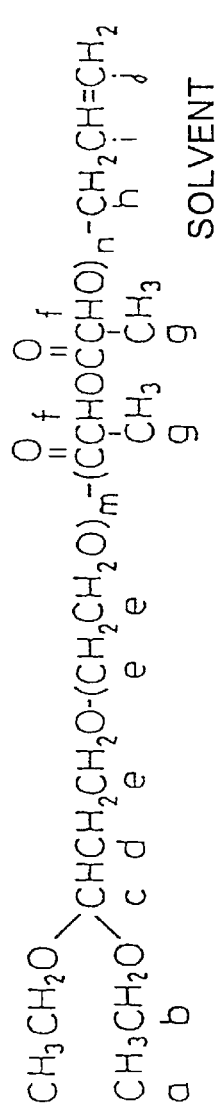
FIG. 6 shows carbon nuclear magnetic resonance spectra of acetal α-terminal/allyl ω-terminal polyethylene oxide/ polylactide block copolymer (the sample of Example 6).
Figure 6:
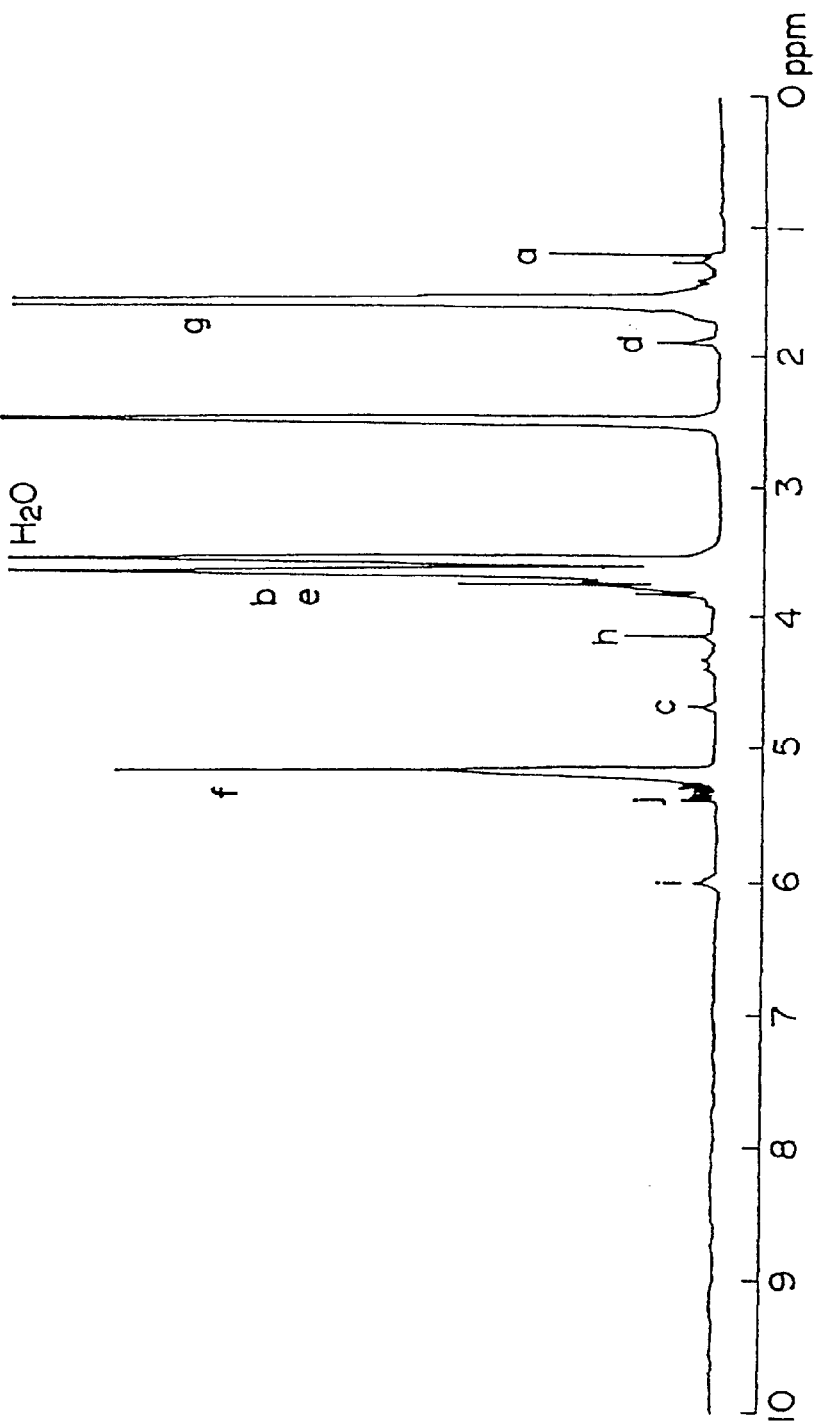

According to the carbon nuclear magnetic resonance spectra in the chloroform deuteride of the polymer attained, the peak originating with the hydroxy group on the ω-terminal of this polymer disappeared completely and instead a peak derived from the allyl group was expressed; the polymer was confirmed to be a heterotelechelic PEO/PL oligomer quantitatively having an acetal group on the α-terminal and an allyl group on the ω-terminal (FIG. 6).

EXAMPLE 7

Potassium naphthalene 0.5 mol/L-tetrahydrofuran solution 2 ml and paratoluene sulfonylchloride 5 g were added to the tetrahydrofuran 20 ml in which the block copolymer sample 1.0 g attained in Example 4 was dissolved and this was agitated for 4 hours at room temperature. The reaction product attained was poured into cold propanol and the polymer was precipitated. The precipitate attained through centrifugal separation was refined by freeze drying from benzene. This yield was 0.95 g (95%). The molecular weight of the polymer attained through gel permeation chromatography was confirmed to be unchanged from before the reaction.

Figure 7:
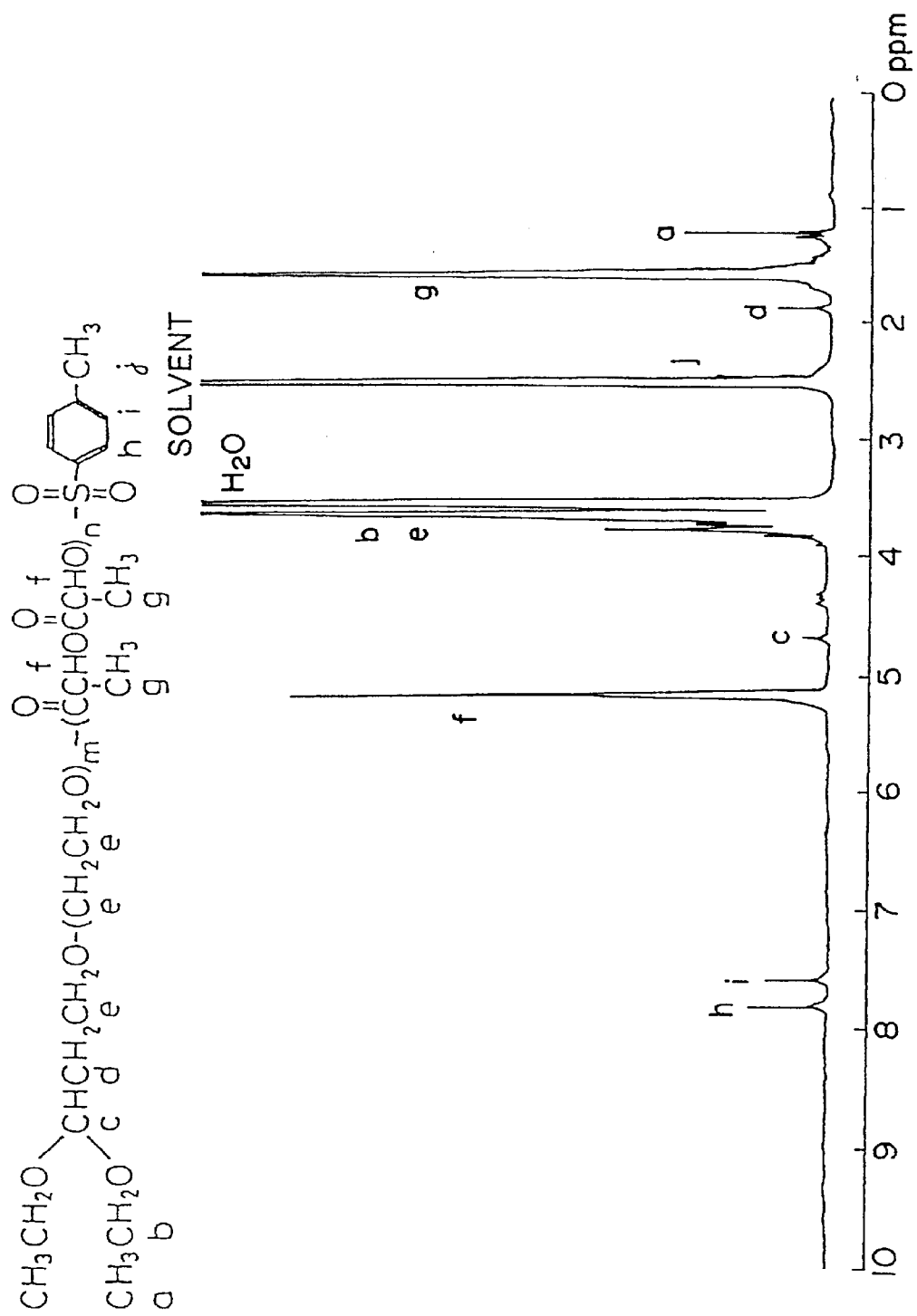
FIG. 7 shows carbon nuclear magnetic resonance spectra of acetal α-terminal/p-toluenesulfonyl ω-terminal polyethylene oxide/polylactide block copolymer (the sample of Example 6).

According to the carbon nuclear magnetic resonance spectra in the chloroform deuteride of the polymer attained, the peak originating with the hydroxy group on the ω-terminal of this polymer disappeared completely and instead a peak derived from the paratoluene sulfonyl group was expressed; the polymer was confirmed to be a heterotelechelic PEO/PL oligomer quantitatively having an acetal group on the α-terminal and a paratoluene sulfonyl group on the ω-terminal (FIG. 7).

EXAMPLE 8

Figure 8:
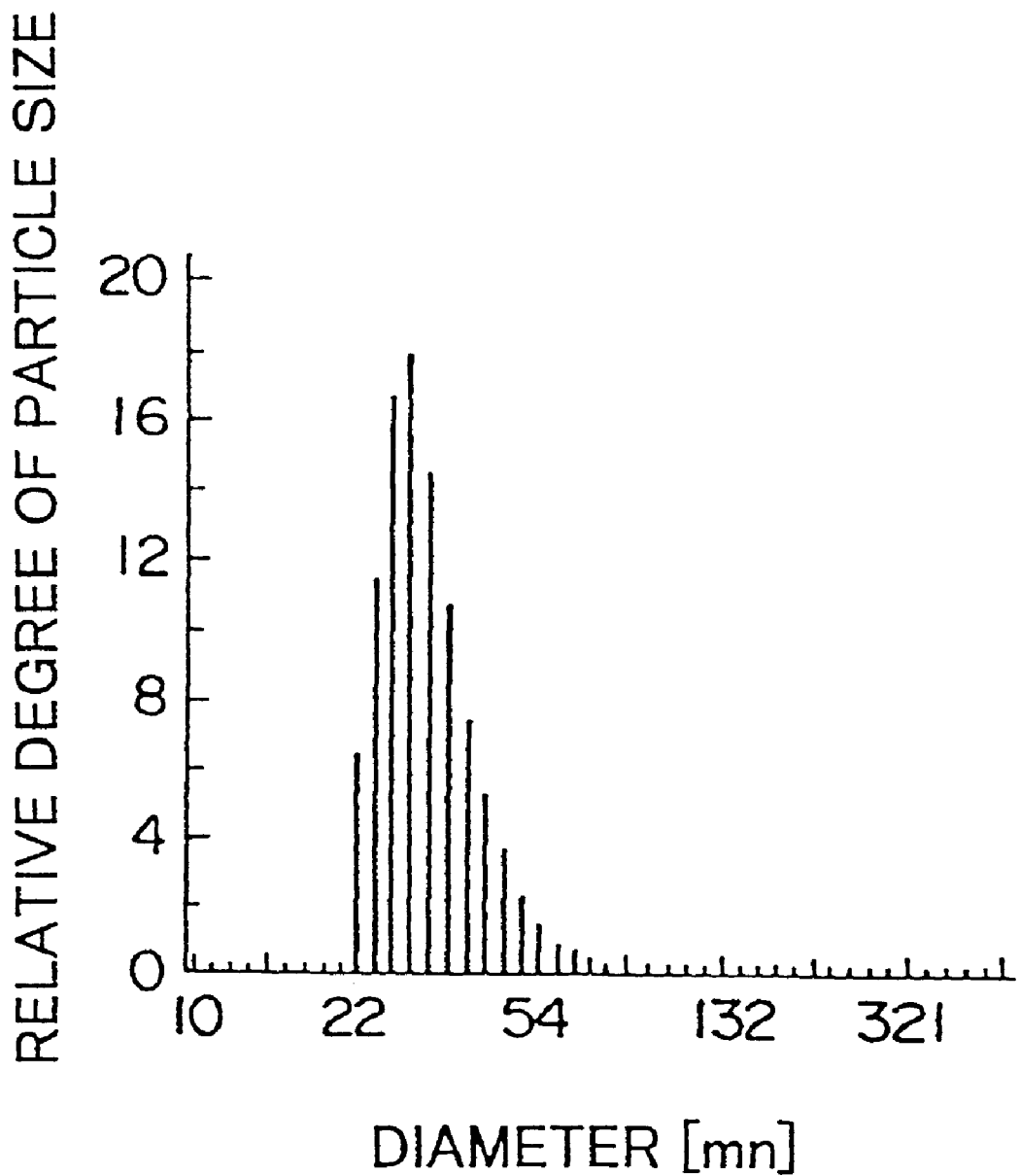
FIG. 8 shows the particle size distribution of high molecular micelle, determined by dynamic laser scattering, in an aqueous solution of aldehyde α-terminal/hydroxy ω-terminal polyethylene oxide/polylactide block copolymer (the sample of Example 4).

The block copolymer 50 mg attained in Example 2 is dissolved in water or an appropriate buffer solution so as to become 0.01–0.1% (w/v). When the micelle formation in these solutions was confirmed with particle size distribution measurement by dynamic light scattering, the formation of a single polymer micelle with average grain diameter 30 nm was confirmed (FIG. 8). The critical micelle concentration of this polymer micelle was 10 mg/L.

EXAMPLE 9

A reactor was charged with 30 ml of THF, 0.13 g of 3, 3-diethoxypropanol and 2 ml solution of potassium naphthalene dissolved in tetrahydrofuran in a concentration of 0.5 mol/L-tetrahydrofuran, and the resulting mixture was stirred for three minutes in an argon atmosphere, and, thus, there was formed a potassium derivative (potassium 3, 3-diethoxypropanoxide) of 3, 3-diethoxypropanol.

There was added 7.0 g of ethylene oxide to the resulting solution, which was then stirred at 1 atm and at a room temperature. After two days-reaction was over, 7.2 g of lactide of lactic acid was added to the reaction liquid, which was then stirred for further one hour. Thus produced solution was poured into cooled propanol so as to precipitate the formed polymer. Centrifugalized precipitate was purified by freeze drying from benzene. The yield was 11.5 g (79%). The polymer obtained by gel permeation chromatography was mono-modal and had a number average molecular weight of 11,000.

Proton nuclear magnetic resonance spectra of the obtained polymer in chloroform deuteride taught that this polymer was a heterotelechelic oligomer which had both units of polyethylene oxide (PEO) and polylactide (PL) and which quantitatively had an acetal group at the α-terminal and a hydroxyl group at the ω-terminal. As for the number average molecular weight of each segment of this block polymer obtained from integral ratio of the spectra, it was 5800 for PEO, and 5100 for PL.

There was dissolved 200 mg of the obtained block polymer into 40 ml of dimethylacetamide, and the resulting solution was dialyzed against water with use of dialytic membrane having a fractional molecular weight of 12,000–14,000 over a period of 24 hours (water was exchanged after 2, 5 and 8 hours, each two liters). Dynamic light scattering measurement of the obtained solution taught that there had bean formed high-molecular micelle having an average particle size of 40 nm. The critical micelle concentration of this micelle was 5 mg/l.

EXAMPLE 10

There was added dropwise 0.1 hydrochloric acid to 10 ml of micelle solution obtained in Example 9 so that pH might be adjusted to 2, and, then, the solution was stirred for two hours at a room temperature. Thereafter, the solution was neutralized with 0.1 N aqueous solution of sodium hydroxide, and, then, the resulting solution was dialyzed against water with use of dialytic membrane having a fractional molecular weight of 12,000–14,000 over a period of 24 hours (water was exchanged after 2, 5 and 8 hours, each two liters). Dynamic light scattering measurement of the obtained solution taught that there had been formed high-molecular micelle having an average particle size of 40 nm. The critical micelle concentration of this micelle was 5 mg/l.

This micelle solution was freeze-dried, and then was dissolved in dimethylsulfoxide deuteride and was subjected to NMR measurement. It was found that the signal derived from acetal group at 1.2 ppm and 4.6 ppm had almost completely disappeared, and there was observed signal derived from hydrogen of carbonyl methylene and hydrogen of aldehyde at 2.7 ppm (t) and 9.8 ppm (s) respectively. From area ratio of the signalk, it was found that 95% of acetal had been hydrolyzed into aldehyde.

EXAMPLE 11

There was dissolved 200 mg of PEO/PL block polymer (number average molecular weight of each segment: PEO: 4,500; PL: 13,000), which had been synthesized in the same manner as in Example 1, into 40 ml of dimethylacetamide, and the resulting solution was dialyzed against water with use of dialytic membrane having a fractional molecular weight of 12,000–14,000 over a period of 24 hours (water was exchanged after 2, 5 and 8 hours, each two liters). Dynamic light scattering measurement of the obtained solution taught that there had been formed high-molecular micelle having an average particle size of 30 nm. The critical micelle concentration of this micelle was 4 mg/l.

INDUSTRIAL APPLICABILITY

This invention provides a heterotelechelic oligomer or polymer which has different functional groups at both ends of its molecule and which has hydrophobic segment and hydrophobic segment in its main chain. It is expected from its constituent components that this oligomer or polymer will show excellent bioavailability. Furthermore, this oligomer or polymer is capable of forming high-molecular micelle which is quite stable in an aqueous solvent.

It is therefore highly possible that the oligomer or polymer can be applied to living organism, or can be utilized in a field wherein a carrier for drug delivery is produced and/or used.

We claim:

1. A heterotelechelic block copolymer which is represented by formula by formula (I) below:

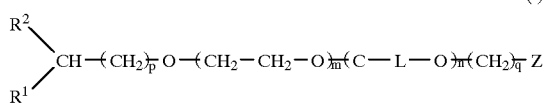

(I)

wherein $R^1$ and $R^2$, combined with each other, denote $C_{1-10}$ alkoxy, aryloxy or aryl-$C_{1-3}$ alkloxy, or $R^1$ and $R^2$ independently denote ethylenedioxy (—O—CH(R')—CH$_2$—O—: therein R'denotes hydrogen atom or $C_{1-6}$ alkyl) which may be substituted with $C_{1-6}$ alky, or, combined with each other, denote oxy (=O), L denotes

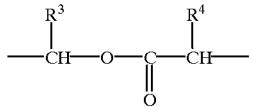

or —(CH$_2$)$_r$— wherein $R^3$ and $R^4$ independently denote hydrogen atom, $C_{1-10}$ alkyl aryl or aryl-$C_{1-3}$ alkyl, and r denotes an integer of 2–5, m denotes an integer of 2–10,000, n denotes an integer of 2–10,000, p denotes an integer of 1–5, q denotes an integer of 0–20, Z denotes, when q is 0 (zero), hydrogen atom, alkali metal, acetyl, acryloyl, methacryloyl, cinnamoyl, p-toluenesulfonyl, 2-mercaptopropionyl or 2-aminopropionyl, or allyl or vinylbenzyl, while, when q is an integer of 1–20, denoting $C_{1-6}$ alkoxycarbonyl, carboxymercapto or amino.

2. The heterotelechelic block copolymer of claim 1 wherein $R^1$ and $R^2$, combined with each other, denote oxy.

3. The heterotelechelic block copolymer of claim 1 wherein $R^1$ and $R^2$ independently denote $C_{1-6}$ alkoxy, phenyloxy or benzyloxy, or, when combined with each other, denote ethylenedioxy which may be substituted with $C_{1-3}$ alkyl.

4. The heterotelechelic block copolymer of claim 1 wherein $R^1$ and $R^2$, combined with each other, denote oxy; and, in L, both $R^3$ and $R^4$ are hydrogen atom or methyl or r denotes an integer of 4; and q denotes an integer of 0–3.

5. The heterotelechelic block copolymer of claim 1 wherein $R^1$ and $R^2$ independently denote $C_{1-6}$ alkoxy; and, in L, both $R^3$ and $R^4$ are hydrogen atom or methyl, or r denotes an integer of 4; and q denotes an integer of 0–3.

6. The heterotelechelic block copolymer of claim 1 wherein m denotes an integer of 10–200, and n denotes an integer of 10–200.

7. The heterotelechelic block copolymer of claim 1 wherein $R^1$ and $R^2$, combined with each other, denote oxy; and, in L, both $R^3$ and $R^4$ are hydrogen atom or methyl, or r denotes an integer of 4; and q denotes 0 (zero); and Z denotes hydrogen atom, acetyl, acryloyl, methacryloyl, cinnamoyl, p-toluenesulfonyl, allyl or vinylbenzyl.

8. The heterotelechelic block copolymer of claim 1 wherein $R^1$ and $R^2$ independently denote $C_{1-6}$ alkoxy; and, in L, both $R^3$ and $R^4$ are methyl or r denotes an integer of 4; and q denotes 0 (zero); and Z denotes hydrogen atom, or sodium, potassium or cesium.

9. The heterotelechelic block copolymer of claim 1 wherein $R^1$ and $R^2$, combined with each other, denote oxy; and, in L, both $R^3$ and $R^4$ are methyl, or r denotes an integer of 4; and q denotes an integer of 1–3; and Z denotes $C_{1-6}$ alkoxycarbonyl, carboxyl, mercapto or amino.

10. A process to produce the heterotelechelic block copolymer of formula (I) of claim 1 which comprises the following steps:

Step (1)

A polymerization initiator represented by the following formula (II)

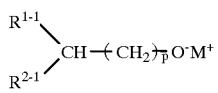 (II)

wherein $R^{1-1}$ and $R^{2-1}$ independently denote $C_{1-10}$ alkoxy, or, combined with each other, denote ethylenedioxy which may be substituted with $C_{1-6}$ alkyl, p denotes an integer of 1–5 and M denotes alkali metal is made to react with ethyleneoxide so that a compound represented by the following formula (III) may be produced:

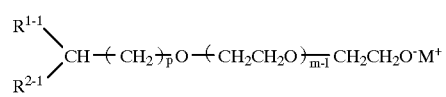 (III)

wherein $R^{1-1}$, $R^{2-1}$, p and M are as defined in formula (II), and m denotes an integer of 2–10,000;

Step (2)

The compound of formula (II) is allowed to react with lactide or lactone which is represented by the following formula (III-a) or (III-b):

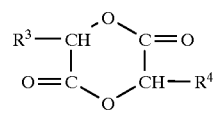 (III-a)

or

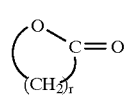 (III-b)

wherein $R^3$ and $R^4$ independently denote hydrogen atom, $C_{1-10}$ alkyl, aryl or aryl-$C_{1-3}$ alkyl, and r denotes an integer of 2–5, so that a bock copolymer represented by the following formula (IV) may be formed:

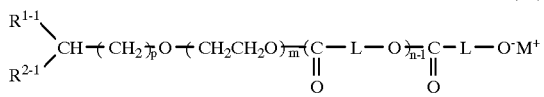 (IV)

wherein

L denotes

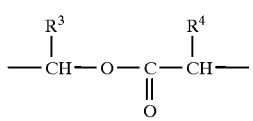

or $-(CH_2)_r-$ and $R^{1-1}$, $R^{2-1}$, p, m, n and M are as defined above;

and, in addition under circumstances,

Step (3)

(i) The alkali metal alkoxide of formula (IV) is selectively hydrolyzed to form a block copolymer of the following formula (V)

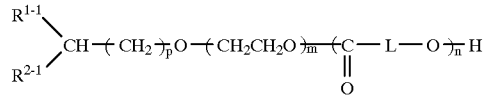 (V)

wherein $R^{1-1}$, $R^{2-1}$, p, m, L and n are as defined above; or (ii) the block copolymer of formula (IV) is completely hydrolyzed to form a block copolymer of the following formula (VI)

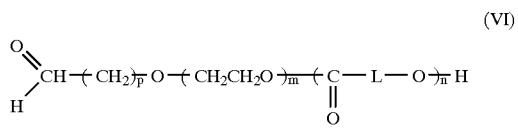 (VI)

wherein p, m, n and L are as defined above;

Step (4)

The block copolymer of formula (V) is allowed to react with (i) acetic acid, acrylic acid, methacrylic acid, cinnamic acid or p-toluenesulfonic acid, or a reactive derivative thereof, or (ii) allyl halide or vinylbenzyl halide, or (iii) a halide represented by the following formula (VII)

 (VII)

wherein X is chlorine, bromine or iodine, q' is an integer of 1–20 and Z' is $C_{1-6}$ alkoxycarbonyl or a protected amino;

and, under circumstances,

Step (5)

The p-toluenesulfonic ester derivative produced in (i) of Step (4) is subjected to transesterification, or the derivatives produced in (i), (ii) or (iii) of Step (4) are subjected to hydrolysis reaction.

11. A high-molecular micelle which comprises the heterotelechelic block copolymer of claim 1 as an active component in an aqueous solvent.

12. The high-molecular micelle of claim 11 wherein Z denotes a group other than alkali metal in the heterotelechelic block copolymer of formula (I) of claim 1.

13. The high-molecular micelle of claim 11 wherein Z denotes a group other than alkali metal while $R^1$ and $R^2$, combined with each other, denote oxy in the heterotelechelic block copolymer of formula (I) of claim 1.

* * * * *